United States Patent [19]

Jaskowski

[11] 4,148,329

[45] Apr. 10, 1979

[54] PROCESS AND COMPOSITION FOR TREATING HAIR

[76] Inventor: Michael C. Jaskowski, 226 Mt. Lebanon Blvd., Pittsburgh, Pa. 15234

[21] Appl. No.: 825,226

[22] Filed: Aug. 17, 1977

[51] Int. Cl.² .............................................. A45D 7/00
[52] U.S. Cl. ............................................ 132/7; 424/71
[58] Field of Search ............................... 132/7; 424/71

[56] References Cited

U.S. PATENT DOCUMENTS 3,650,280  3/1972  Roberts ..................................... 132/7

Primary Examiner—G. E. McNeill

Attorney, Agent, or Firm—Webb, Burden, Robinson & Webb

[57] ABSTRACT

The hair shaping composition or fixative includes a straight chain dialdehyde having from 2 to 6 carbon atoms, preferably glyoxal in amounts from 0.5 to 10% by weight, as the active ingredient. The relaxer includes from 1 to 15% by weight trisodium phosphate as the active ingredient. The process for treating the hair comprises cleaning the hair, applying the relaxer thoroughly to the hair, heating the hair until the desired relaxation is achieved, rinsing the relaxed hair, applying the fixative thoroughly from the roots to the tips of the hair, heating the hair, rinsing the hair and thereafter styling the rinsed hair, if desired.

13 Claims, No Drawings

PROCESS AND COMPOSITION FOR TREATING HAIR

FIELD OF THE INVENTION

My invention relates to processes and compositions for treating hair and, more particularly, to a process and composition for shaping hair and primarily for hair which requires straightening.

DESCRIPTION OF THE PRIOR ART

Hair shaping treatments such as straightening are normally conducted by licensed beauticians. The primary reason for this is that the compositions currently being used can be harmful to the skin and scalp as well as the hair, if not properly employed. These compositions contain potentially harmful ingredients such as sodium hydroxide (lye) as the active ingredient.

Where sodium hydroxide is utilized, the treatments cannot be applied directly to the scalp and, therefore, the hair roots are not properly treated thereby lessening the duration of the effectiveness of the treatment. Because of the potential hazards involved with using sodium hydroxide base hair treatments, such treatments are limited to specific age groups and hair types which are less susceptible to the potential burning of the sodium hydroxide base solution and damaging effects upon the hair.

Many attempts have been made to develop compositions for treating hair which are substantially less harmful, but these various compositions have not proven effective in breaking down the necessary components in the hair for subsequent shaping.

Representative prior art patents include U.S. Pat. Nos. 3,973,574; 3,951,156; 3,946,749; 3,910,289; 3,902,507; 3,728,447; 3,654,936; 3,650,280; 3,193,463 and 3,148,126. Certain of these patents include teachings relative to the utilization of glyoxal or glycolates or other associated compounds of glyoxylic acid, but none of these patents teaches using the glyoxal as the active ingredient for shaping hair after it has been previously relaxed.

SUMMARY OF THE INVENTION

My invention can be used as a hair straightener or as a curl producer (commonly known as permanent waving). It further can be used on tinted, dyed or bleached hair and it is safe to normal skin. Because it is safe to normal skin, my hair treatment is effective all the way down to the hair roots since the scalp need not be protected. Hair damage such as by breakage is virtually eliminated.

Periodic conditioning treatments such as oiling are not required since the natural oil is sufficient to maintain healthy hair. My treatment lasts for a substantial duration and no reversion to the original condition occurs with the treated hair. Because of the safeness of my method and composition, there is virtually no age limit to the subjects being treated nor to the type of hair which will receive the treatment. Further, the novice as well as the professional can administer the treatment.

My process for treating hair includes the utilization of a hair shaping composition including a straight chain dialdehyde having from 2 to 6 carbon atoms (preferably glyoxal) as the active ingredient. Preferably the relaxer includes trisodium phosphate as the active ingredient. The method includes shampooing the hair and rinsing, applying the relaxer thoroughly from the roots to the tips of the hair, heating, rinsing thoroughly, applying the straight chain dialdehyde, fixative or shaping ingredient thoroughly from the roots to the tips of the hair, heating, rinsing and then styling, if desired. After applying the relaxer and fixative respectively, heat is normally applied to assist in the reactions. This heat can be applied through a hot pressing comb or by a standard dryer such as an infrared dryer.

DESCRIPTION OF THE PREFERRED EMBODIMENTS

Human hair is composed of a protein called keratin. Keratin molecules are made up of amino acid chains which can be thought of as a ladder-like chemical structure. One of the rungs of the ladder-like structure is cystine which includes a disulfide double bond. Keratin is very resistant to chemical change and this is why problems have been encountered heretofore in treating hair. In addition, each strand of hair consists of three spearate layers, the cuticle, the cortex and the medulla. The chemical changes that take place in the hair are normally made in the cortex layer which is the intermediate layer. Therefore, the porosity of the cuticle layer (the outer layer) is important since it determines the amount of treating agent which can enter the cortex.

I have found that I can break down the so-called ladder structure of the keratin by breaking certain of the bonds which represent the rungs of the ladder structure and thereafter reform the resultant structure into a stabilized form.

Specifically, I have found that human hair can be broken down through the use of a hair relaxer in which trisodium phosphate is the active ingredient. It is believed that the active ingredient swells the hair and breaks down the disulfide double bond of the cystine portion of the keratin molecule. The amount of trisodium phosphate can be varied depending upon the type of human hair involved. Generally, this range will be from 1 to 15 weight percent with the lower amounts being applicable to easy to manage caucasian hair and the upper limit being applicable to tightly curled negro or negroid hair.

The key to my hair treatment process is the reforming of the keratin molecule to form a stable structure after it has been broken down by the relaxer. I have found that the fixative to accomplish this should include a straight chain dialdehyde having from 2 to 6 carbon atoms. The preferable dialdehyde is glyoxal. The utlization of dialdehydes having more than six carbons results in a certain amount of steric hindrance thereby causing a loss of effectiveness in reforming the keratin molecule. The preferred limits of the glyoxal are .5 to 10% by weight of the fixative. The lower limit represents a minimum required amount and the upper limit of 10% represents a practical limit since I have found that amounts over 10% are generally wasted and not necessary. It is believed that the glyoxal reacts with the amine groups and carboxyl groups which result from the breakdown of the cysteine and then further to sulfhydrylpropionic acid and aminoethyl mercaptan.

My process of treating hair is as follows. The hair is first cleaned such as by a pretreatment shampoo of high viscosity. An example of such shampoo is as follows.

Weight Percentage

3% trisodium phosphate
40% sodium lauryl sulfate
5% Varamide MA-1

Trace - odorant
Trace - colorant
0.25% Tergitol NPX
51.75% water (softened or demineralized)

Varamide MA-1 is the trade name of a coconut oil diethanolamide manufactured by Ashland Chemical Co. Tergitol NPX is the trade name of a penetrant-wetting agent manufactured by Union Carbide Corporation.

This shampoo will initiate the swelling of the hair through the inclusion of the trisodium phosphate.

After shampooing and rinsing, the relaxer is applied thoroughly to the hair from the roots to the hair tips. The amount of time the relaxer remains on the hair depends upon the hair condition especially the degree of coarseness where the hair is being straightened during treatment. An example of my relaxer is as follows.

Weight Percentage 6.0% trisodium phosphate
0.25% Tergitol NPX
2.0% K-15 MS Methocel
Trace - odorant
Trace - colorant
91.75% water (softened or demineralized)

K-15 MS Methocel is the trade name of a thickening agent (hydroxypropyl methylcellulose) manufactured by the Dow Chemical Co. and having a viscosity of 15,000 centipoise.

It should be noted that softened or demineralized water is preferred so that the various active ingredients work on the hair itself rather than enter into side reactions with impurities found in the water. For example, trisodium phosphate is a known water softener and side reactions will take place if the water is not demineralized.

The reaction of the relaxer, that is, the reaction of the trisodium phosphate in breaking the bonds of the keratin molecule can be hastened by the application of heat. The heat can be applied in one of several ways known in the art. Where the operator has the time and the attention capabilities, the relaxer can be combed into the hair from the roots to the tips of the hair using a wide spaced toothed comb. A comb could then be used of the variable heat hot pressing type and should be operated using the maximum comfortable temperature setting until the desired straightness is obtained. Alternatively, the relaxer can be combed thoroughly into the hair using a wide spaced toothed comb. Thereafter, an elastomeric cap is placed over the hair and the maximum heat acceptable is applied using a hair dryer such as an infrared dryer. Heating is not essential and if time permits, the necessary reactions will take place at body temperatures. After this particular treatment, the pH of the hair will be approximately 10 to 12 although pH control is not necessarily critical to my process.

Thereafter the hair is rinsed thoroughly and the fixature is applied from the roots to the tips of the hair using the wide spaced toothed comb. A sample of my fixative is as follows.

Weight Percentage 0.20% aluminum sulfate
10.0% glyoxal
0.25% Tergitol NPX
Trace - odorant
Trace - colorant
2.0% K-15 MS Methocel
87.55% water (softened or demineralized)

The aluminum sulfate acts as a catalyst to the glyoxal and it is preferred that the aluminum sulfate be present in amounts of 2 parts catalyst to 100 parts of glyoxal.

After the fixative has been thoroughly applied from the roots to the tips of the hair, heat is once again applied in either of the manners described hereinabove for the relaxer. It has been found that the application of heat is more essential after the fixative than after the relaxer. Approximately 10 minutes is a normal time to complete the fixing cycle once the fixative has been thoroughly applied.

Where straight hair is to be waved, standard curlers are applied during the heating cycle to give the desired permanent. Thereafter, the hair is thoroughly rinsed and may be styled if desired with the utilization of a cream rinse, hot iron or other styling technique. The hair after the fixative and the heating will have a pH of approximately 2 to 4. It has been found that the glyoxal fixative is the critical ingredient in my process of shaping hair. In fact, the glyoxal fixative will restore other relaxers by in effect repairing or stabilizing the so-called rungs as well as the long chain portions of the keratin molecule. It will be recognized that the fixative and relaxer can be applied either as a solution or in cream lotion form. The glyoxal fixative will also provide body to thin hair as well as repair hair previously damaged by the use of harmful or improperly applied relaxers. It will also be recognized that in addition to the specified active ingredients set forth hereinbefore, additional ingredients, such as thickeners, fillers, surfactants, foaming agents, buffering agents and the like can be included in arriving at a particular hair treating composition.

Hair shaping treatments in accordance with my invention have been successfully applied to a number of different hair types and styles. The treatment has proven to be effective in each instance while at the same time being safe and long lasting.

I claim:

1. A hair shaping composition including an active ingredient comprised of a straight chain dialdehyde having from 2 to 6 carbon atoms.

2. The composition of claim 1, said dialdehyde being glyoxal.

3. The composition of claim 2, said glyoxal being present in a weight percent of .5 to 10.0.

4. The composition of claim 3, said composition including a catalyst present in substantially the amount of about 2 parts catalyst per 100 parts of glyoxal, a thickening agent and the balance water.

5. The composition of claim 4, said catalyst being aluminum sulfate.

6. The composition of claim 3 comprising by weight about 10% glyoxal, .20% aluminum sulfate, .25% wetting agent, 2.0% hydroxypropyl methylcellulose and the balance demineralized water.

7. In a process for treating human hair including a hair relaxing step and a hair shaping step, the improvement comprising subjecting said hair to a hair shaping composition including a straight chain dialdehyde having from 2 to 6 carbon atoms as the active ingredient.

8. The proces of claim 7, said improvement including subjecting said hair to a hair relaxer having from 1 to 15 percent by weight trisodium phosphate as the active ingredient, said dialdehyde being glyoxal present in a weight percentage of .5 to 10.

9. A process for treating human hair comprising:

A. cleaning the hair;
B. applying a relaxer containing trisodium phosphate as the active ingredient thoroughly to the hair;
C. rinsing the relaxed hair;
D. applying a fixative including glyoxal as the active ingredient thoroughly to the relaxed hair;
E. heating the hair until a desired shaping is achieved; and
F. rinsing the hair.

10. The process of claim 9 including heating the hair after applying the relaxer until a desired hair relaxation is achieved.

11. The process of claim 10 including covering the hair with an elastomeric cap subsequent to the relaxer application step and prior to the heating step.

12. The process of claim 9, said heating step C comprising combing the hair with a hot comb.

13. The process of claim 9, said trisodium phosphate being present in a weight percent of 1 to 15 and said glyoxal being present in a weight percent of .5 to 10.0.